United States Patent [19]

Yamanisi et al.

[11] 4,251,629
[45] Feb. 17, 1981

[54] DETERMINATION OF HYDROGEN PEROXIDE

[75] Inventors: Kazuhiko Yamanisi, Tokyo; Kuniaki Tokuda; Tosiro Hanada, both of Kawagoe, all of Japan

[73] Assignee: Wako Pure Chemical Industries, Ltd., Osaka, Japan

[21] Appl. No.: 928,804

[22] Filed: Jul. 28, 1978

[30] Foreign Application Priority Data

Jul. 29, 1977 [JP] Japan .................................. 52-90989

[51] Int. Cl.$^3$ ........................ C12Q 1/28; G01N 31/00
[52] U.S. Cl. .................................... 435/28; 23/230 B; 252/408; 435/10; 435/11; 435/12; 435/14; 435/20
[58] Field of Search ...... 252/408 R; 195/99, 103.5 R, 195/103.5 C, 103.5 U; 23/230 B, 230 M; 435/14, 12, 11, 10, 20, 28

[56] References Cited

U.S. PATENT DOCUMENTS

| 3,886,045 | 5/1975 | Meiattini | 435/14 |
|---|---|---|---|
| 3,979,262 | 9/1976 | Hunziker | 435/10 |

OTHER PUBLICATIONS

Kabasakalian et al., "Enzymatic Blood Glucose Determination by Colorimetry of N,N-Diethylaniline-4-Aminoantipyrine, *Clin. Chem.*, vol. 20, No. 5, (1974), pp. 606–607.

Takayama et al., "A New Enzymatic Method for Determination of Serum Cholin-Containing Phospholipids," *Clin. Chem. Acta*, vol. 79, (1977), pp. 93–98.

Eisenstaedt, "The Condensation of Aminoantipyrine with Aromatic Amines in the Presence of Oxidizing Agents," *J. Org. Chem.*, vol. 3, (1939), pp. 153–165.

*Primary Examiner*—Thomas G. Wiseman
*Attorney, Agent, or Firm*—Armstrong, Nikaido, Marmelstein & Kubovcik

[57] ABSTRACT

Colorimetrical determination of hydrogen peroxide in clinical examinations, food additives analyses and general analyses can be carried out accurately, rapidly and economically by using a composition for producing color producing reagents comprising 4-aminoantipyrine, a N-substituted-3-alkylaniline and a hydrogen peroxide activating agent such as peroxidase, said composition forming a coloring material having excellent sensitivity and color stability in contact with hydrogen peroxide.

10 Claims, No Drawings

DETERMINATION OF HYDROGEN PEROXIDE

This invention relates to a composition for producing color producing reagents for determining hydrogen peroxide, and a method for determining hydrogen peroxide by using said composition.

Recently enzymological analysis in clinical examinations has been used widely due to highly evaluated specificity.

As a method for determining glucose, uric acid, cholesterol, choline esterase, phospholipid, creatine or creatinine in a body fluid, there are prosperously employed methods for determining the desired substance by determining hydrogen peroxide produced by, for example, acting its oxidation enzyme or acting an oxidation enzyme on the reaction product obtained in the course of the enzyme reaction.

These hydrogen peroxide determining methods can roughly be divided into the following methods:

(Ia) a method comprising transforming a chromogen to an oxidation type color developed material by enzymic action of peroxides and measuring optical absorbance of the color developed material, (Ib) a method comprising oxidatively condensing one or two chromogens by enzymic action of peroxidase to produce a color developed material and measuring optical absorbance of the color developed material, (II) a method comprising either acting catalase in the presence of an alcohol and introducing the aldehyde produced into a color developing system, or acting aldehyde dehydrogenase in the presence of NAD and measuring the amount of NADH produced.

In the method (Ia), as chromogens, there have been used o-tolidine, 2,7-diaminofluorene, N,N-dimethyl-p-phenylenediamine, o-dianisidine, o-aminophenol, and the like.

In the method (Ib), as chromogens, there have been used a combination of 4-aminoantipyrine with phenol or N,N-dimethylaniline or N,N-diethylaniline, a combination of 3-methyl-2-benzothiazolinone hydrazone with o-tolidine or N,N-dimethylaniline or N,N-diethylaniline, or 4-methoxy-1-naphthol or its derivatives which can form a dimer. These chromogens alone or in combination are used as color producing reagents for determining the hydrogen peroxide.

On the other hand, optimum activation pH of the oxidation enzyme which oxidatively decomposes the desired substance is distributed widely, usually in the range of about pH 5 to 9. If the optimum activation pH is not identical with or not very close to optimum pH of the clor developing reaction, accuracy of the measurement, simplicity and quickness of the operation and economy of the method cannot be maintained.

For example, optimum activation pH of uricase which is derived from yeast and is an oxidation enzyme for uric acid is pH 7.5–8.5, but there is no suitable color producing reagent which has sensitivity necessitated at that pH and can maintain color stability. Therefore, the determination of uric acid is carried out, either by conducting the uricase reaction and the oxidation reaction or oxidative condensation reaction separately at different pH and measuring, or by using a large amount of uricase to measure at a low pH, or by using a large amount of sample and a color producing reagent having low sensitivity and optimum color developing pH of 7–8 and measuring. But these methods are not so good in the accuracy and economy.

In order to overcome these defects of the conventional methods, the present inventors have studied eagerly color producing reagents for determining hydrogen peroxide by catalyzing or participating a hydrogen peroxide activating agent and found that when special N-substituted-3-alkylanilines are used as a color producing agent which is to be condensed with 4-aminoantipyrine which has been evaluated as being the most reliable, the resulting color producing reagents afford excellent sensitivity and color stability at an extremely wide pH range and stability of the reagents by themselves is also excellent, and accomplished this invention.

SUMMARY OF THE INVENTION

This invention provides a composition for producing color producing reagents for determining hydrogen peroxide which comprises
4-aminoantipyrine,
a N-substituted-3-alkylaniline of the formula:

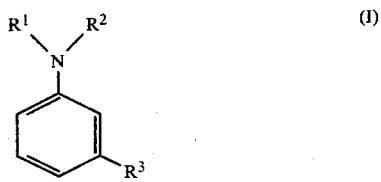

wherein $R^1$ and $R^2$ are independently a lower alkyl group or a hydroxyalkyl group having 1 to 5 carbon atoms; and $R^3$ is a lower alkyl group, and
a hydrogen peroxide activating agent.

This invention also provides a method for determining colorimetrically hydrogen peroxide by using said composition which comprises using 4-aminoantipyrine in combination with a N-substituted-3-alkylaniline of the formula:

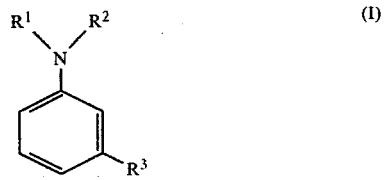

wherein $R^1$ and $R^2$ are independently a lower alkyl group or a hydroxyalkyl group having 1 to 5 carbon atoms; and $R^3$ is a lower alkyl group, in the presence of a hydrogen peroxide activating agent to form a coloring material, in contact with hydrogen peroxide and measuring the amount of the resulting coloring material.

DETAILED DESCRIPTION OF THE INVENTION

In the N-substituted-3-alkylaniline of the formula (I), the lower alkyl group includes an alkyl group having preferably 1 to 5 carbon atoms such as methyl, ethyl, propyl, isopropyl, etc. Examples of the hydroxyalkyl group having 1 to 5 carbon atoms are hydroxymethyl, hydroxyethyl, hydroxypropyl, and the like.

Examples of the N-substituted-3-alkylanilines of the formula (I) are N-methyl-N-hydroxymethyl-3-methylaniline, N-ethyl-N-hydroxyethyl-3-methylaniline, N-ethyl-N-hydroxyethyl-3-ethylaniline, N-methyl-N-hydroxyethyl-3-methylaniline, N-methyl-N-hydroxypropyl-3-methylaniline, N-ethyl-N-hydroxypropyl-3- methylaniline, N-methyl-N-hydroxyethyl-3-ethylaniline, N-propyl-N-hydroxyethyl-3-methylaniline, N-methyl-N-hydroxyethyl-3-propylaniline, N,N-bis(β-hydroxyethyl)-3-methylaniline, N,N-bis(β-hydroxypropyl)-3-methylaniline, N,N-dimethyl-3-methylaniline, N,N-dimethyl-3-ethylaniline, N,N-dimethyl-3-propylaniline, N,N-diethyl-3-methylaniline, N,N-diethyl-3-ethylaniline, N,N-dipropyl-3-methylaniline, and the like. Any N-substituted-3-alkylanilines having the formula (I) as defined above can afford excellent sensitivity and color stability. Particularly N-ethyl-N-hydroxyethyl-3-methylaniline can afford the best sensitivity.

Even if the 2-position (ortho position) or the 4-position (para position) of N-substituted anilines is substituted with a lower alkyl group, no satisfactory results can be obtained in sensitivity and color stability.

The N-substituted-3-alkylaniline of the formula (I) is usually used in an amount of from about 1 to 20 moles per mole of 4-aminoantipyrine.

The hydrogen peroxide activating agent used in this invention includes not only peroxidase but also tungstic acid and its salts, molybdic acid and its salts, a mixture of an iodide and one of these inorganic compounds, ions of iron, copper, cerium, and vanadic acid, and the like. A catalytic amount of the hydrogen peroxide activating agent is usually used in the composition of this invention.

The N-substituted-3-alkylaniline of the formula (I), which is a color producing agent in this invention, is oxidatively condensed with 4-aminoantipyrine in contact with $H_2O_2$ to produce an indophenol type dyestuff of the formula (II) having maximum absorption near $\lambda = 545$ nm as shown below:

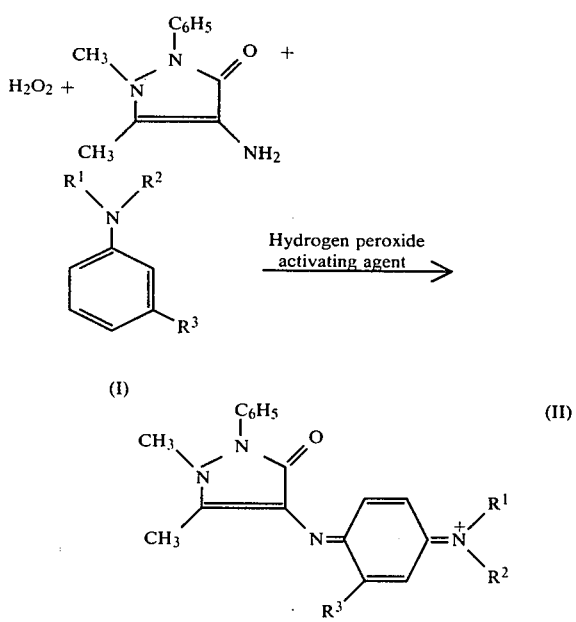

When the composition of this invention is used, remarkably excellent sensitivity and color stability over an extremely wide pH range can be obtained in contact with hydrogen peroxide as shown in Table 1 contrary to the known combined use of 4-aminoantipyrine and phenol in which color developing and color stability are limited to the range of pH 7–9 and the known combined use of 4-aminoantipyrine and dimethylaniline or diethylaniline in which color developing and color stability are limited to the range of pH 4–6.

TABLE 1

| | Color producing agent (λmax) | | pH 3 | pH 4 | pH 5 | pH 6 | pH 7 | pH 8 | pH 9 |
|---|---|---|---|---|---|---|---|---|---|
| Color producing agents of this invention | N-Ethyl-N-hydroxyethyl-3-methylaniline (545 nm) | Sensitivity | 96 | 98 | 100 | 100 | 100 | 99 | 97 |
| | | Color stability | 98 | 99 | 99 | 99 | 98 | 97 | 81 |
| | N,N-Dimethyl-3-methylaniline (545 nm) | Sensitivity | 93 | 95 | 96 | 96 | 95 | 90 | 87 |
| | | Color stability | 92 | 99 | 100 | 100 | 98 | 92 | 78 |
| | N,N-Bis(β-hydroxyethyl)-3-ethylaniline (545 nm) | Sensitivity | 29 | 39 | 39 | 41 | 41 | 41 | 36 |
| | | Color stability | 82 | 95 | 99 | 100 | 100 | 97 | 82 |
| Conventional color producing agents | Phenol (505 nm) | Sensitivity | 11 | 22 | 31 | 40 | 42 | 42 | 41 |
| | | Color stability | 21 | 37 | 63 | 82 | 98 | 98 | 96 |
| | N,N-Dimethylaniline (545 nm) | Sensitivity | 79 | 85 | 85 | 84 | 80 | 71 | 56 |
| | | Color stability | 95 | 100 | 100 | 98 | 82 | 63 | 45 |

In Table 1, the values at the lines of color stability show each ratio of absorbance in percent after 90 minutes based on the absorbance at the complete color development (100%) and the values at the lines of sensitivity show each ratio of absorbance in percent based on the absorbance of N-ethyl-N-hydroxyethyl-3-methylaniline at the pH showing the maximum sensitivity (100%).

In Table 1, typical examples of the color producing agents used in this invention are listed, but needless to say the same excellent results can also be obtained as to other N-substituted-3-alkylanilines having the formula (I) as defined above.

Using the following sample and color producing reagent solutions, absorbance is measured in the following manner to obtain the data in Table 1:

Method for measuring:
A mixture containing 50 μl of a sample and 5 ml of a color producing reagent solution is allowed to stand at room temperature for 5 minutes and subsequently absorbance at each maximum absorption wavelength (λmax) is measured.

Sample:
A hydrogen peroxide solution: $H_2O_2$ 5 mg/dl
Color producing reagent solution:
To a buffer solution obtained by using a buffer agent as shown in Table 2 for each pH, 2000 units of peroxidase, 0.5 millimole of 4-aminoantipyrine and 5 millimoles of a color producing agent as listed in Table 1 are added and the total amount is adjusted to 1 liter.

TABLE 2

| pH | 3 | 4 | 5 | 6 | 7 | 8 | 9 |
|---|---|---|---|---|---|---|---|
| Buffer agent | Acetate (0.1 M) | | | Phosphate (0.1 M) | | Borate (0.1 M) | |

As mentioned above, the optimum color developing pH range for the composition, that is, the combined color producing reagents to form a coloring material used in this invention is so wide that a pH to be employed can be selected only by considering other factor, for example, optimum activation pH of an oxidation enzyme to be used. This means, for example, that in the case of determining glucose in serum by using glucose oxidase having optimum activation pH at pH 5, pH 5 can be employed; in the case of determining cholesterol in serum by using cholesterol oxidase having optimum activation pH at about pH 5.8, about pH 6 can be employed; and in the case of determining uric acid in serum by using uricase having optimum activation pH at pH 7.5–8.5, about pH 8 can be employed. This results in making the method of determining hydrogen peroxide of this invention more accurate, rapid and economical.

The color producing agent having the best sensitivity is N-ethyl-N-hydroxyethyl-3-methylaniline. The combined use of N-ethyl-N-hydroxyethyl-3-methylaniline and 4-aminoantipyrine is about 2.5 times as sensitive as the combined use of phenol and 4-aminoantipyrine as shown in Table 1. Such high sensitive color producing agents as N-ethyl-N-hydroxyethyl-3-methylaniline and N,N-dimethyl-3-methylaniline are preferably used for determining uric acid, creatinine, free cholesterol and the like which are present in serum in very small amounts.

On the other hand, N-substituted-3-alkylanilines of the formula (I) having relatively low sensitivity such as N,N-dihydroxyethyl-3-methylaniline are preferably used for determining glucose, total cholesterol, choline esterase, phospholipid, and the like which are present in serum in large amounts.

The N-substituted-3-alkylaniline of the formula (I) is very stable in the form of a solution of about pH 6 or less, but it can be used, if required, as a salt thereof such as mineral acid salts, e.g. hydrochlorides, sulfates, etc. or organic acid salts, or can be used as powder, or as processed solid such as tablets, freeze-dried products, and the like together with other components, if necessary.

When the composition of this invention is used for a method for determining hydrogen peroxide, the method can be conducted at a pH in the range of pH 3–9. Further, the composition of this invention can be used not only for clinical examinations but also for analyses of food additives, and general analyses.

This invention is illustrated more particularly by way of the following examples but, as will be more apparent, is not limited to the details thereof.

EXAMPLE 1

Determination of Uric Acid

In 100 ml of 0.1 M phosphate buffer solution (pH 8.0), 10 units of uricase, 100 units of peroxidase, 30 mg of 4-aminoantipyrine and 100 mg of N-ethyl-N-hydroxyethyl-3-methylaniline are dissolved to produce a color producing reagent solution.

In a test tube, 100 μl of serum and 3 ml of the color producing reagent solution are placed and allowed to stand at 37° C. for 10 minutes. Subsequently absorbance at 546 nm and 600 nm is measured both on the sample and a reagent blank, and differences of absorbance are obtained. A uric acid concentration in the serum is calculated by using a calibration curve previously prepared according to the conventional method.

EXAMPLE 2

Determination of Glucose

In 100 ml of 0.1 M acetate buffer solution (pH 5.0), 400 units of glucose oxidase, 200 units of peroxidase, 30 mg of 4-aminoantipyrine and 100 mg of N,N-bis(β-hydroxyethyl)-3-methylaniline are dissolved to produce a color producing reagent solution.

In a test tube, 20 μl of serum and 3 ml of the color producing reagent solution are placed and allowed to stand at 37° C. for 10 minutes. Subsequently absorbance at 545 nm is measured both on the sample and a reagent blank, and difference of absorbance is obtained. A glucose concentration in the serum is calculated by using a calibration curve previously prepared according to the conventional method.

EXAMPLE 3

Determination of Total Cholesterol

In 100 ml of 0.2 M phosphate buffer solution (pH 5.8), 15 units of cholesterol oxidase, 20 units of cholesterol ester hydrase, 150 units of peroxidase, 10 mg of 4-aminoantipyrine, 100 mg of N,N-dimethyl-3-methylaniline, and 150 mg of Triton X-100 (a trade-mark, Rohm & Haas Co.) are dissolved to produce a color producing reagent solution.

In a test tube, 10 μl of serum and 3 ml of the color producing reagent solution are placed and allowed to stand at 37° C. for 10 minutes. Subsequently absorbance at 545 nm is measured both on the sample and a reagent blank, and difference of absorbance is obtained. A total cholesterol concentration in the serum is calculated by using a calibration curve previously prepared according to the conventional method.

EXAMPLE 4

Determination of Total Cholesterol

In 100 ml of 0.2 M phosphate buffer solution (pH 5.8), 15 units of cholesterol oxidase, 20 units of cholesterol ester hydrase, 0.5 g of sodium tungstate, 1.0 g of sodium iodide, 10 mg of 4-aminoantipyrine, 100 mg of N,N-dimethyl-3-methylaniline and 150 mg of Triton X-100 are dissolved to produce a color producing reagent solution.

In a test tube, 10 μl of steam and 3 ml of the color producing reagent solution are placed and allowed to stand at 37° C. for 10 minutes. Subsequently absorbance at 545 nm is measured both on the sample and a reagent blank, and difference of absorbance is obtained. A total cholesterol concentration in the serum is calculated by using a calibration curve previously prepared according to the conventional method.

Sensitivity and color stability in Examples 1 to 4 are as shown in Table 3.

TABLE 3

| Example No. | Substance examined (pH) | Sensitivity of standard solution | Color stability |
|---|---|---|---|
| 1 | Uric acid (8.0) | Standard soln: uric acid 10 mg/dl Sensitivity: 0.135 (λ546 nm/-600 nm) | 98% (90 min/10 min) |
| 2 | Glucose | Standard soln: glucose | 100% |

TABLE 3-continued

| Example No. | Substance examined (pH) | Sensitivity of standard solution | Color stability |
|---|---|---|---|
| | (5.0) | 200 mg/dl Sensitivity: 0.403 (λ545 nm) | (90 min/10 min) |
| 3 | Total cholesterol (5.8) | Standard soln: cholesterol 200 mg/dl Sensitivity: 0.227 (λ545 nm) | 100% (90 min/10 min) |
| 4 | Total cholesterol (5.8) | Standard soln: cholesterol 200 mg/dl Sensitivity: 0.227 (λ545 nm) | 100% (90 min/10 min) |

Note
Absorbance is measured by using a Hitachi 101 type spectrophotometer.

What is claimed is:

1. A composition for producing color producing reagents for determining hydrogen peroxide which comprises
4-aminoantipyrine,
a N-substituted-3-alkylaniline of the formula:

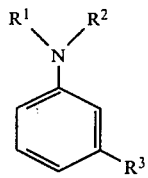

(I)

wherein $R^1$ is a member selected from the group consisting of a lower alkyl group having 1 to 5 carbon atoms and a hydroxyalkyl group having 1 to 5 carbon atoms; $R^2$ is a member selected from the group consisting of a lower alkyl group having 1 to 5 carbon atoms and a hydroxyalkyl group having 1 to 5 carbon atoms and $R^3$ is methyl, ethyl or propyl, and an agent for activating hydrogen peroxide.

2. A composition according to claim 1, wherein in the formula (I) $R^1$ is a lower alkyl group having 1 to 5 carbon atoms and $R^2$ is a hydroxyalkyl group having 1 to 5 carbon atoms.

3. A composition according to claim 1, wherein in the formula (I) $R^1$ and $R^2$ are the same or different alkyl groups having 1 to 5 carbon atoms.

4. A composition according to claim 1, wherein in the formula (I) $R^1$ and $R^2$ are the same or different hydroxyalkyl groups having 1 to 5 carbon atoms.

5. A composition according to claim 1, wherein the N-substituted-3-alkylaniline is N-ethyl-N-hydroxyethyl-3-methylaniline.

6. A composition according to claim 1, wherein the N-substituted-3-alkylaniline is N,N-dimethyl-3-methylaniline.

7. A composition according to claim 1, wherein the N-substituted-3-alkylaniline is N,N-bis(β-hydroxyethyl)-3-ethylaniline.

8. A composition according to claim 1, wherein the agent for activating hydrogen peroxide is peroxidase.

9. A composition according to claim 1, wherein the agent for activating hydrogen peroxide activating agent is a mixture of an iodide and one compound selected from the group consisting of tungstic acid and its salts, molybdic acid and its salts.

10. In a method for determining hydrogen peroxide in an enzymatic reaction system wherein 4-aminoantipyrine is oxidatively condensed with an aniline to produce a color developed material and the optical absorbance of the color developed material is determined, the improvement comprising employing an N-substituted-3-alkylaniline of the formula:

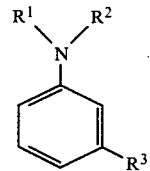

wherein $R^1$ is a member selected from the group consisting of a lower alkyl group having 1 to 5 carbon atoms and a hydroxyalkyl group having 1 to B 5 carbon atoms; $R^2$ is a member selected from the group consisting of a lower alkyl group having 1 to 5 carbon atoms and a hydroxyalkyl group having 1 to 5 carbon atoms and $R^3$ is methyl, ethyl or propyl, in the presence of an agent for activating hydrogen peroxide.

* * * * *